United States Patent [19]
Wile

[11] Patent Number: 5,819,993
[45] Date of Patent: Oct. 13, 1998

[54] STICK MEDICAMENT DISPENSING DEVICE

[76] Inventor: Jonathan B. Wile, 211 Sherbrook Ave., Williamsville, N.Y. 14221

[21] Appl. No.: 708,811

[22] Filed: Sep. 9, 1996

[51] Int. Cl.$^6$ ................................................. A45D 40/06
[52] U.S. Cl. ........................... 222/390; 604/289; 401/72; 132/320
[58] Field of Search .................. 604/289, 292, 604/309, 310; 132/318, 320, 73, 73.5; 401/68, 72, 175; 222/390

[56] References Cited

U.S. PATENT DOCUMENTS

| | | | |
|---|---|---|---|
| 2,328,973 | 9/1943 | Goldfisher | 222/575 X |
| 2,336,328 | 12/1943 | Whalen | 123/320 X |
| 3,062,222 | 11/1962 | Quinn | 132/320 |
| 3,612,704 | 10/1971 | Marchant | 401/175 |
| 3,917,417 | 11/1975 | Lang | 401/72 |
| 5,085,352 | 2/1992 | Sasaki et al. | 222/390 X |

*Primary Examiner*—Kenneth Bomberg
*Attorney, Agent, or Firm*—Crossetta & Associates

[57] ABSTRACT

A dispensing device is disclosed which generally comprises an elongate cylindrical container adapted to hold an elongate cylindrical stick medicament composition, having an open end sized and shaped to generally conform to a cross-section contour along a human finger, and a shaping cap which covers the open end and comprises a convex inner surface enabled for shaping the stick medicament.

6 Claims, 2 Drawing Sheets

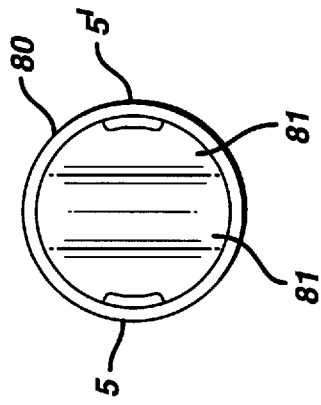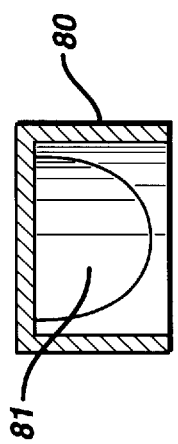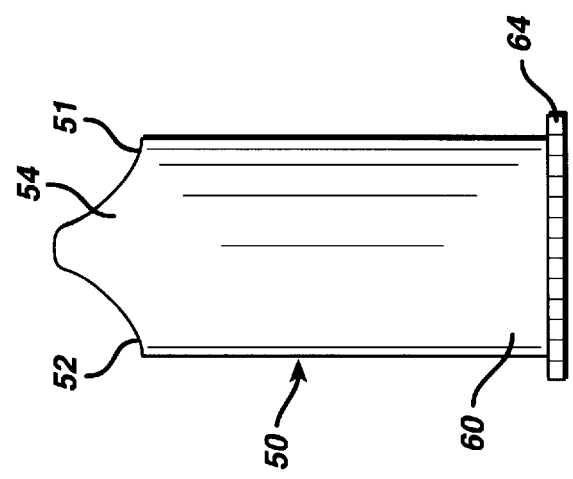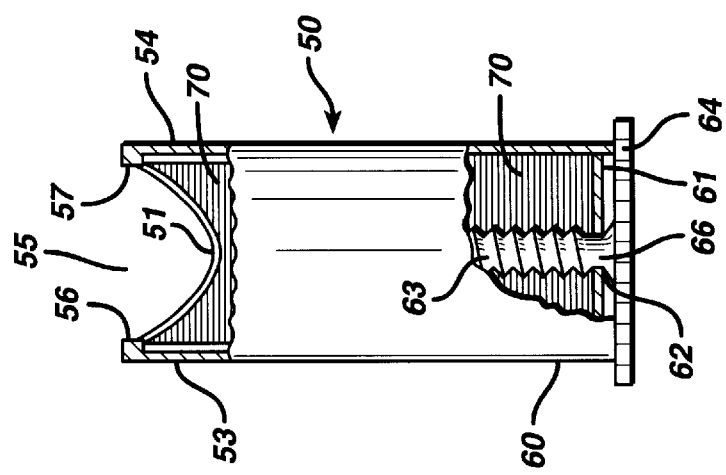

STICK MEDICAMENT DISPENSING DEVICE

This invention relates to a device for dispensing a stick medicament, cosmetic, lubricant or the like for controlled application to a creased, crinkled, ridged or the like skin surface. The device has particular utility as a convenient dispenser of a medicament control stick composition to skin areas adjacent finger, thumb and toe nail areas.

BACKGROUND OF THE INVENTION

Devices for dispensing stick compositions for use on the human body are known in the prior art, particularly those developed for dispensing cosmetic or anti-chapping compositions to the lips and for the application of deodorants and the like to under-arm areas.

Dispensing devices used in the prior art to apply reusable stick compositions to the human body generally comprise a means for gradually extending and/or retracting the stick composition telescopically through an opening of a hollow dispenser to a point where the composition can be applied as desired on the lips or under-arm skin surface.

One lipstick dispensing device of the prior art, disclosed in U.S. Pat. No. 2,336,328, comprises a sleeve which encases a cylindrical lipstick composition. The lipstick is pushed from the sleeve, which has an acute shaped notch, that shapes the stick composition at its outlet from the device by allowing the composition to wear down during use and conform to the shape of the notch. Another lipstick dispensing device of the prior art, disclosed in U.S. Pat. No. 3,062,222, is cylindrical and has an opening having a convexly curved edge with concave edges adjacent thereto which form a shaped notch to enable the lipstick composition to be shaped at its outlet by wearing down the composition during use.

Frequently, it is desirable to apply a stick medicament or cosmetic to other areas of the human body other than the under-arms or lips. Variations in weather, frequent hand-washing and the like can create problems with skin chapping in humans, a condition which can be painful and irritating. Those who enjoy the winter sports wherein their hands and/or feet may be exposed to temperature and humidity variations, frequently experience a condition of chapping about the finger and/or toe cuticles wherein the skin dries and/or splits causing an open lesion or the like which is painful and/or irritating. Guarding against and treating a chapping condition typically involves periodic application of a lotion or the like to the problem skin area, a process which is inconvenient, generally requires carrying a bulky container or the like and generally involves application over large skin areas when the problem is specific to ridges and creases in the skin area adjacent the finger and/or toe cuticles.

Anti-chapping stick composition devices, made for application to lips, are frequently effective in relieving the pain of chapping in other skin areas, however since the devices provided for dispensing the product are specifically designed for application of a stick composition to lips, they are neither convenient nor efficient for use in application of the stick composition to ridges and crevices adjacent the nails.

An object of the present invention is to provide a device which is compact and convenient for dispensing stick compositions to crevices and ridges of human skin.

Another object of the present invention is to provide a dispensing device which shapes the application surface of a stick composition being dispensed to a desirable shape.

A still further object of the invention is to provide a device for dispensing anti-chapping stick composition which can shape the application surface of the composition to generally conform to skin surfaces adjacent the nails of a human.

These and other objects of the invention will become apparent from the following description of the embodiments.

SUMMARY OF THE INVENTION

The dispensing device of the present invention generally comprises an elongate cylindrical container, adapted to hold an elongate cylindrical stick medicament composition, having an open end for measured ejection of the stick composition, an opposite base end comprising means for manually ejecting and retracting the stick composition through the open end, a forming end and a shaping cover for shaping the surface of the composition at the open end.

The forming end of the container of the invention is comprised of two elongations, curved along the perimeter of the container and arranged at the open end of the cylindrical container opposite each other. The elongations are preferably constructed by forming two deep notches at opposite sides of the end of the cylinder, sized and shaped to generally conform to the cross-sectional contour of an average human finger tip, skin ridge or the like.

The shaping cover comprises a cylindrical cap which is sized to fit over the open end of the cylindrical container and cap the open end containing the elongations. The shaping cover comprises an inner curved surface which traverses the cylindrical container diameter, extending from notch to notch into the open end, which is sized and shaped to generally mate with the opposing notches. The inner curved surface can reshape a stick composition upon insertion of the cap.

In a preferred embodiment, one or more of the curved elongations at the open end of the container comprise a convex rounded, inward projection at about its tip. Such projection serves at least two functions, first being to engage the stick composition along its cylindrical surface to resist turning of the cylindrical stick composition in the cylindrical container as it is being ejected, and second to provide a convex rounded surface for engaging the skin and/or nails, which is spaced from the concave rounded inner surface of the elongations. Such rounded surface enables a desirable wear pattern of the stick composition by providing a comfortable leading surface for engaging a tender chapped area of skin and creating a defined space, along the inner surface of the curved elongations, which enables accumulation of stick composition for application to the skin.

Means for manually ejecting and retracting the stick composition from the opening at the end of the cylindrical container, are well known in the prior art. Preferable means generally include screw means or the like which engages a base of the cylindrical container and moves the stick composition inwardly and outwardly from the container by turning the screw means. In a preferred embodiment a screw is rotatably mounted in a base of the container and the head of the screw comprises a knurled plate. The body of the screw engages the stick composition. Rotating the head or knurled plate rotates the screw into or out of the stick composition. The stick composition is prevented from rotating by the inward projection(s) of the curved elongations, the screw is prevented from axial movement within the container by its mount to the base and the stick composition moves inwardly or outwardly depending upon the direction of rotation of the screw.

Though the device of the invention has preferable utility in the application of a stick medicament or the like to ridged surfaces of skin, particularly the finger and toe nails, it can also be used for application to other ridged areas of the body and can comprise a non-pharmaceutical stick composition such as a cosmetic and the like.

BRIEF DESCRIPTION OF THE DRAWINGS

FIG. 2 comprises a front partial sectional view of another dispensing device of the invention.

FIG. 3 comprises a side elevational view of the dispensing device of FIG. 2.

FIG. 4 comprises a bottom plan view of a shaping cap of the invention.

FIG. 5 comprises a partial sectional, side view of a shaping cap of FIG. 4 taken along about line 5—5'.

DETAILED DESCRIPTION OF THE INVENTION

Figure 1:
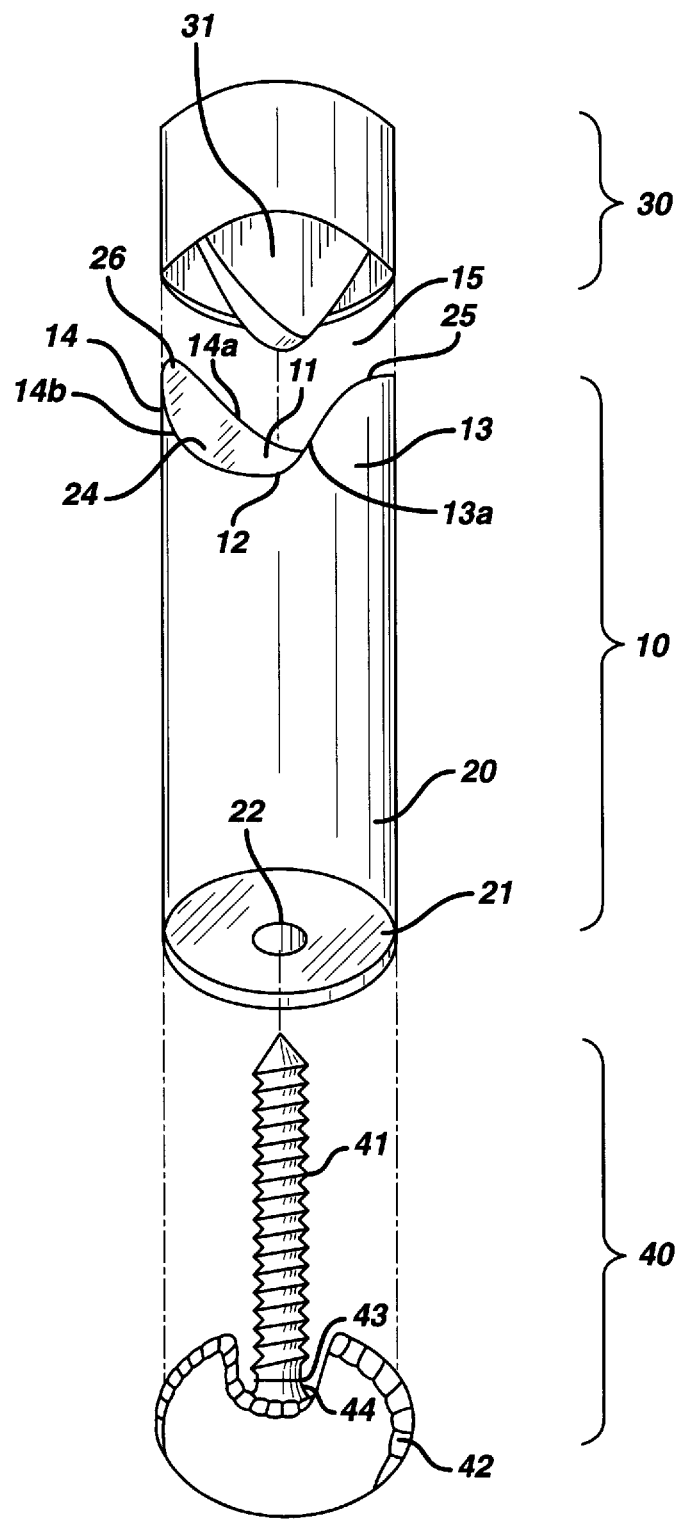
FIG. 1 comprises an exploded, partially sectioned, perspective view of a dispensing device of the invention.

Referring now to the FIG. 1, wherein a dispensing device of the invention is illustrated as comprising a hollow cylindrical container 10, a shaping cap 30 and a stick composition ejector assembly 40.

Container 10 is illustrated as having open end 15 and base end 20. Open end 15 comprises deep curved notches 11 and 12, which are arranged therein to form opposing elongations 13 and 14. Elongations 13 and 14 are integral with container 10 and are curved along the perimeter of container 10 at open end 15. Edges 13a and 13b (not shown) and 14a,14b of the elongations are curved in accord with notches 11 and 12. Elongations 13 and 14 comprise inner surfaces 24 and 23 (not shown) and tips 25 and 26 respectively.

In FIG. 1, base end 20 of container 10 is illustrated as comprising a base 21 containing a central hole 22, the base engaging base end 20 of the cylinder in such manner as to be fixed from moving.

Ejector assembly 40 is illustrated as comprising threaded shaft 41 and knurled head 42. Shaft 41 is threaded to engage a mating hole in the stick composition (not shown) and comprises a retaining lip 43. In the illustrated embodiment, the ejector assembly is formed from an elastomeric composition, with threaded shaft 41 being sized to screw into central hole 22 of base 21. Retaining lip 43 is sized to be larger than central hole 22, but is comprised of an elastic material and engineered for forcible insertion through hole 22 to be resistant to reverse removal therefrom. Collar 44 of shaft 41 is sized to enable free rotation of the ejector assembly in hole 22 of base 21, such that upon assembly, the ejector assembly can rotate clockwise or counterclockwise without axial movement through the hole. In operation, a composition stick having a hole aligned with the central hole mates with the threaded shaft, such that rotation of the threaded shaft enables ejection and/or retraction of the stick composition from the open end of the container.

Cap 30 comprises an inner, convex curved surface 31 which is shaped at opposite sides to be in general mating alignment with notches 11 and 12, such that upon engaging the cylindrical end of the stick composition will form a curved slot in the end generally conforming to the shape around an average finger tip.

In FIGS. 2 and 3, an embodiment of the invention is illustrated wherein container 50 comprises open end 55 and base end 60. Open end 55 comprises deep curved notches 51 and 52, which are arranged therein to form opposing elongations 53 and 54. Elongations 53 and 54 are integral with container 50 and are curved along its perimeter. Elongations 53 and 54 comprise inward projections 56 and 57 which are illustrated in this embodiment as being arranged at about the tips of the inner surfaces of the elongated projections. In the illustrated embodiment, inward projections 56 and 57 are shown as comprising rounded, convex surfaces.

Base end 60 of container 50 is illustrated as comprising a base 61 containing a central hole 62. The ejector is illustrated as comprising threaded shaft 63 and knurled head 64. Shaft 63 is threaded to engage a mating hole in stick composition 70. In the illustrated embodiment, the threaded shaft is formed from an elastomeric composition, which deforms to forcibly insert through central hole 62 of base 61 and be retained to freely rotate within central hole 62 at collar 66. In operation, composition stick 70, is self-tapped by installation of the threaded shaft and rotation of the threaded shaft enables ejection and/or retraction of the stick composition from the open end of the container.

In FIGS. 4 and 5, cap 80 is illustrated as comprising an inner, convex curved surface 81 which is shaped at opposite sides to be in general mating alignment with notches in the container such as for example notches 51 and 52 of FIGS. 2 and 3, such that upon engaging the cylindrical end of the stick composition it will form a curved slot in the end generally conforming to the shape around an average finger edge.

It should be understood that while the invention has been illustrated and described as embodied for use with an anti-chapping composition, it is not intended to be limited to the details shown.

I claim:

1. A stick medicament composition dispensing device comprising:

an elongate hollow cylindrical container, having an open end for ejection of a stick medicament composition and an opposite end;

said open end of said container having a perimeter comprising opposing notches arranged to form opposing curved elongations extending longitudinally from said open end to tips, said opposing curved elongations being sized and shaped to generally mate with a contour along a curved surface of a human;

said device further comprising said stick medicament composition, cylindrically shaped and arranged in said cylindrical container for axial longitudinal ejection and retraction through said open end;

means for ejecting and retracting said stick composition through said open end;

wherein said tips of said curved elongations comprise an inward projection having a surface, said surface being rounded and convex in a plane crossing a longitudinal axis of the dispensing device, and arranged to engage said curved surface of a human.

2. The device of claim 1 wherein said ridge is about the shape of an end of a human finger.

3. The device of claim 1 comprising a cylindrical shaping cover, sized to fit over said elongations and cap said open end of said cylindrical container, said cover having an inner convexly curved surface arranged to traverse a diameter of said cylindrical container and shaped to mate with said opposing notches.

4. The device of claim 1 wherein said means for manually ejecting and retracting said stick composition from the open end of said cylindrical container, comprises a screw means.

5. The device of claim 4 wherein a screw means is rotatably mounted through a base of said container and engages said stick composition.

6. The device of claim 1 wherein said stick medicament comprises a skin chapping medicament.

* * * * *